US 6,444,614 B2

(12) United States Patent
Dean

(10) Patent No.: US 6,444,614 B2
(45) Date of Patent: Sep. 3, 2002

(54) ASPARTIC ACID DERIVATIVE-CONTAINING COMPOSITIONS AND USE THEREOF IN STIMULATING AND/OR REGULATING PLANT AND PLANT PRECURSOR GROWTH

(75) Inventor: Frank W. Dean, Spring, TX (US)

(73) Assignee: LidoChem Inc., Hazlet, NJ (US)

( * ) Notice: Subject to any disclaimer, the term of this patent is extended or adjusted under 35 U.S.C. 154(b) by 0 days.

(21) Appl. No.: 09/829,395

(22) Filed: Apr. 10, 2001

Related U.S. Application Data

(60) Provisional application No. 60/196,436, filed on Apr. 12, 2000.

(51) Int. Cl.[7] .......................... A01N 37/02; A01N 43/38
(52) U.S. Cl. ........................................ 504/138; 504/147
(58) Field of Search .................................. 504/147, 138

(56) References Cited

U.S. PATENT DOCUMENTS

| | | | | |
|---|---|---|---|---|
| 5,733,858 A | | 3/1998 | Wilson et al. ............... | 510/361 |
| 5,846,925 A | | 12/1998 | Wilson et al. ............... | 510/400 |
| 6,107,518 A | | 8/2000 | Groth et al. ................. | 562/571 |
| 6,127,329 A | * | 10/2000 | Baillely et al. ............. | 510/320 |
| 6,184,182 B1 | | 2/2001 | Gillespie et al. ............ | 504/116 |

FOREIGN PATENT DOCUMENTS

| | | |
|---|---|---|
| JP | 09-136807 | 5/1997 |
| JP | 11-29415 | 2/1999 |

OTHER PUBLICATIONS

Monograph #4849, "Indolebutyric acid", The Merck Index, 10th Edition, 1983, published by Merck and Co., Inc., Rahway, NJ, p. 720.

* cited by examiner

*Primary Examiner*—S. Mark Clardy
(74) *Attorney, Agent, or Firm*—Michaelson & Wallace; Peter L. Michaelson; Arthur L. Liberman

(57) ABSTRACT

Described is the use, [in the absence of (a) fertilizers and (b) Periodic Table Group IIa and greater Group metal cations and chelated metals], of aqueous solutions of the N-substituted aspartic acids, (i) N-(1,2-dicarboxyethyl) aspartic acid ['IDS'] and (ii) N,N'-1,2-ethanediylbis-aspartic acid ['EDDS'], ammonium salts, alkali metal salts, ammonium-alkali metal salts and optical isomers thereof in stimulating or regulating the growth of a living, growing plant precursor [germinating seed] or plant [from the 'seedling stage' to the 'late-maturity stage']. Such use, optionally, is in the presence of aditional adjuvants free from fertilizer as well as Periodic Table Group IIa and greater metal Group cations and chelated metals. Also described are novel compositions comprising (a) the 'IDS' and/or ammonium, alkali metal, ammonium-alkali metal salts thereof as well as optical isomers thereof in admixture with (b) the 'EDDS' and/or ammonium, alkali metal and ammonium-alkali metal salts thereof as well as optical isomers thereof.

31 Claims, 12 Drawing Sheets

ASPARTIC ACID DERIVATIVE-CONTAINING COMPOSITIONS AND USE THEREOF IN STIMULATING AND/OR REGULATING PLANT AND PLANT PRECURSOR GROWTH

RELATED CO-PENDING APPLICATION

This application is based-in-part on co-pending Provisional Patent Application Serial No. 60/196,436 filed on Apr. 12, 2000, and expiring on Apr. 12, 2001, benefit for which is claimed under 35 USC 119(e).

BACKGROUND OF THE DISCLOSURE

1. Field of the Invention

The present invention is directed towards stimulating or regulating the growth of a living, growing plant precursor (germinating seed) or plant (from the 'seedling stage' to the 'late maturity' stage) in the absence of (a) fertilizer and (b) Periodic Table Group IIa and greater Group metal cations and chelated metals.

The present invention is also directed to novel compositions of matter comprising (i) N-(1,2-dicarboxyethyl) aspartic acid (hereinafter also referred to as 'iminodisuccinic acid' or 'IDS'), it's ammonium salts, alkali metal salts, ammonium-alkali metal salts and optical isomers thereof in admixture with (ii) N,N'-1,2-ethanediylbis-aspartic acid (hereinafter also referred to as 'ethylenediamine-disuccinic acid' or 'EDDS'), it's ammonium salts, alkali metal salts, ammonium-alkali metal salts and optical isomers thereof. Such mixture also may comprise 1H-indole-3-butanoic acid (hereinafter also referred to as 'indolebutyric acid' or 'IBA') as well as additional adjuvants.

2. Description of the Prior Art

The prior art recognizes the use of biodegradable metal chelates of such polyamino succinic acids as EDDS (such as iron, copper, zinc and manganese chelates) in plant nutrition, for the express purpose of supplying such metals in plant nutrition. Specifically, U.S. Pat. No. 5,733,858 issued on Mar. 31, 1998 and having an effective filing date of Aug. 30, 1995 (Wilson et al I) and the continuation-in-part thereof, U.S. Pat. No. 5,846,925 issued on Dec. 8, 1998 (Wilson et al II) state:

"The invention includes the use of iron complexes of a polyaminodisuccinic acid and a polyaminomonosuccinic acid in abatement of hydrogen sulfide and other gases and as a source of iron in plant nutrition. Similarly other complexes such as the copper, zinc and manganese complexes supply those trace metals in plant nutrition. The ferrous complexes are also useful in nitrogen oxide abatement." (Col. 5, lines 57–64 of Wilson et al I and Col. 5, lines 60–67 of Wilson et al II).

The prior art also recognizes the advantage of using Periodic Table Group IIa (and greater Groups) metal-complexed IDS for use as 'trace nutrient fertilizer(s)'. Specifically, U.S. Pat. No. 6,107,518 issued on Aug. 22, 2000 (effective date, Apr. 4, 1997) (Groth et al) states:

"The invention relates to a process for the preparation of iminodisuccinic acid alkali metal salts . . . The resulting products can be employed as complexing agents for alkaline earth metal and heavy metal ions in the fields of . . . agriculture . . . In these fields, use as a nutrient fertilizer . . . is to be emphasized in particular . . ." (Col. 1, lines 5–15 of Groth et al).

The use of amino acids with good biodegradability (particularly in conjunction with fertilizers such as 'N-P-K' fertilizer) having one of the structures as set forth in FIGS. 24 and 25, described herein, infra, in the 'BRIEF DESCRIPTION OF THE DRAWINGS' section, including EDDS as well as its alkaline earth metal salts or salts of transition metals, as a 'plant growth factor for agriculture and horticulture' is described in Japanese Published Kokai No. 11-29415 (A) published on Feb. 2, 1999 (Takahashi et al) and abstracted in Chemical Abstracts, Volume 130:120927g.

Specifically, claim 2 of the Takahashi et al Kokai reads as follows:

"2. Plant growth factor for agriculture and horticulture characterized by containing at least one of the following compounds . . . their alkaline earth metal salts or salts of transition metals . . .' (structure set forth as FIG. 24, infra) . . .' where symbols are defined as follows: $W^1$ indicates an alkylene group containing 1–6 carbon atoms possibly substituted by hydroxide groups, $R^1$ and $R^2$ independently indicate alkyl groups with 1–4 carbon atoms under the provision that the group can contain a hydrogen atom, alkyl group containing 1–6 carbon atoms, hydroxyl group or carboxyl group: . . .' (Structure set forth as FIG. 25, infra)' . . . Where symbols are defined as follows: $R^3$ indicates an alkyl group containing 1–4 carbon atoms possibly substituted by a hydrogen atom, alkyl group with 1–6 carbon atoms, hydroxyl group or carboxyl group, and $R^4$ and $R^5$ groups independently indicate alkyl groups containing 1–4 carbon atoms possibly substituted by a hydrogen atom, hydroxyl group or carbonyl group, under the provision that $R^4$ and $R^5$ cannot simultaneously be hydrogen atoms."

Furthermore, in paraphrasing Application Example 1 of Takahashi et al, Chem. Abstracts 130:120927(1999) states:

" . . . Lettuce seeds were cultured in a fertilizer soln. contg. 100 ppm S,S-ethylenediamine-N,N-disuccinic acid (the stability const. 8.63, the biodegradability 98%) to show good plant growth."

The prior art also recognizes that indolebutyric acid (IBA), suitably diluted, is useful for promoting and accelerating root formation of plant clippings (Monograph #4849, page 720, 'The Merck Index', $10^{th}$ edition, 1981).

The use of IDS and/or EDDS or ammonium salts, alkali metal salts, ammonium-alkali metal salts or organic amine salts, it's optical isomers thereof in the absence of any (a) fertilizer (e.g., 'N-P-K') and (b) Periodic Table Group IIa (or 'greater' Group) cations or chelated metals of our invention is neither expressly nor implicitly disclosed by the aforementioned prior art; and such use, as described herein, is unobvious, unexpected and advantageous.

Furthermore the novel compositions of matter of our invention comprising IDS and EDDS as well as salts thereof and optical isomers thereof (taken alone, or further together with indolebutyric acid and/or other 'adjuvants') are neither explicitly nor implicitly disclosed in the prior art, and the properties thereof, as living plant precursor and living plant growth stimulants or regulators are unexpected, unobvious and advantageous.

Thus, a need exists in the art for the use of a fertilizer-free and Periodic Table Group IIa and greater Group metal cation and chelated metal-free IDS and/or EDDS (and/or ammonium salts, alkali metal salts, ammonium-alkali metal salts and/or optical isomers thereof) composition for stimulating or regulating the growth of plant precursors (germinating seeds) or plants (from the 'seedling stage' to the 'late maturity' stage). 'Periodic Table Group IIa and greater Group' metals include, but are not limited to alkaline earth metals, (e.g., calcium, magnesium, barium and strontium), manganese (Group VIIb), zinc (Group IIb), Copper (Group Ib) and iron (Group VIIIb). The term 'ammonium' is herein intended to include the $NH_4^+$ cation as well as the $HO-CH_2-CH_2-NH_3^+$ (also indicated herein as '2-hydroxyethylammonium') cation.

SUMMARY OF THE INVENTION

Accordingly, an object of the invention is to provide for the use of a fertilizer-free and Periodic Table Group IIa and greater Group metal cation-free and chelated metal-free IDS and/or EDDS (and/or ammonium salts, alkali metal salts, ammonium-alkali metal salts and/or optical isomers thereof) composition for stimulating or regulating the growth of plant precursors (germinating seeds) or plants (from the 'seedling stage' to the 'late maturity' stage).

Another object of the invention is to provide novel compositions of matter, particularly and unexpectedly and advantageously useful for stimulating or regulating the growth of plant precursors (germinating seeds) and plants (from the 'seedling stage' to the 'late maturity' stage) comprising (a) IDS, ammonium salts, alkali metal salts and/or optical isomers thereof and (b) EDDS, ammonium salts, alkali metal salts, ammonium-alkali metal salts and/or optical isomers thereof, taken alone or further together with indolebutyric acid ('IBA') and/or other adjuvants.

These and other objects are achieved by my invention as set forth hereinbelow.

My invention thus provides a process for stimulating or regulating the growth of a living, growing plant precursor (germinating seed) or plant having a degree of maturity of from about >0% (seedling stage) up to about <100% (late maturity stage) of full growth consisting of the steps of:

(a) Formulating an aqueous plant growth-regulating or stimulating solution consisting essentially of water, substantially free of any Periodic Table Group IIa or higher Group metal cations or chelated metals, and at least one substantially pure nitrogen-containing organic compound selected from the group consisting of IDS, EDDS, ammonium salts thereof, alkali metal salts thereof, ammonium-alkali metal salts thereof and optical isomers thereof;

(b) Providing a living, growing (i) plant precursor, or (ii) plant having a degree of maturity of from about >0% up to about <100% of full growth; and (c) Applying, in the absence of fertilizer, a plant precursor or plant growth stimulating or regulating concentration and quantity of said nitrogen-containing organic compound contained in said plant precursor or plant growth-regulating or growth-stimulating solution to said plant precursor or to said plant or to the proximity of said plant precursor or said plant over a period of time and at a rate such that the growth of the plant precursor or plant is regulated or stimulated.

Optionally, the step (a) of formulating the aqueous plant growth-regulating or stimulating solution also includes (prior to the step of application to the plant precursor or plant, or proximity thereof) the simultaneous admixing or immediately-subsequent admixing of the aqueous solution with an adjuvant selected from the group consisting of:

(a) carriers;
(b) surfactants;
(c) carbon skeleton energy adjuvants;
(d) vitamin/co-factor adjuvants;
(e) gums;
(f) anti-microbial agents;
(g) buffers;
(h) protective colloids; and
(i) viscosity modifiers.
(j) growth regulators Examples of such adjuvants (in addition to indolebutyric acid ('IBA') are set forth herein, infra.

Examples of the chemical structures of the IDS and EDDS salts useful in the practice of my invention are set forth in FIGS. 15–21, inclusive, infra, and described in the section herein entitled: 'BRIEF DESCRIPTION OF THE DRAWINGS', infra.

The living, growing plants and plant precursors of our invention are monocotyledons and dicotyledons, as exemplified by:

I. Monocotyledons
(a) *Allium cepa* var. *proliferum* Targioni-Tozzetti (shallot);
(b) *Curcuma domestica* Val. (turmeric);
(c) *Dioscorea opposita* Thunb. (wild yam);
(d) *Ellettaria cardamomum* Maton (cardamom);
(e) *Oryza perennis* Moench (wild rice);
(f) *Phalaenopsis amablis* Blume (moth orchid);
(g) *Phoenix dactylifera* L. (date palm);
(h) *Polianthes tuberosa* L. (tuberose);
(i) *Saccharum officinarum* L. (noble sugar cane);
(j) *Vanilla fragrans* (Salisb.) Ames (vanilla);
(k) *Vetiveria zizanoides* (L.) Nash (khuskhus grass);
(l) *Zea mays* L. (field corn);
(m) *Zea mays* L. var. saccharata (sweet-corn).

II. Dicotyledons
(a) *Cinnamomum cassia* (Nees) Nees ex Blume (cassia);
(b) *Coffea canephora* Pierre ex Froehner (arabica coffee);
(c) *Cananga odorata* (Lam.) Hook.f.&Thoms. (ylang-ylang);
(d) *Dipteryx Schreb.odorata* (Aubl.) Willd. (tonka bean);
(e) *Durio Adans. zibethinus* Murr. (durian);
(f) *Glycine max.* (L.) Merr. (soya bean);
(g) *Gossypium hirsutum* L. (cotton);
(h) *Mentha spicata* L. (spearmint);
(i) *Nicotiana suaveolens* Lehm. (nicotine tobacco);
(j) *Ocimum basilicum* L. (sweet basil);
(k) *Passiflora edulis* Sims (passion fruit);
(l) *Persea americana* Mill. (avocado);
(m) *Petunia violacea* Lindl. (petunia);
(n) *Phaseolus vulgaris* L. (snap bean);
(o) *Pueraria thunbergiana* (Sieb.&Zucc.) Benth. (kudzu);
(p) *Cuphea hyssopifolia* Kunth. (Mexican heather).

When the nitrogen containing compounds useful in the practice of our invention include alkali metal salts, the preferred alkali metal salts are potassium salts and sodium salts, as exemplified by the compounds having the structures as set forth in FIGS. 15–19, infra, as described in the section herein entitled: 'BRIEF DESCRIPTION OF THE DRAWINGS', infra.

The optical isomers useful in the practice of our invention have structures, for example, as set forth in FIGS. 22 and 23 herein, described in the section herein entitled 'BRIEF DESCRIPTION OF THE DRAWINGS', infra.

When using the novel composition of our invention, containing the (a) IDS and/or salts or optical isomers thereof and (b) the EDDS and/or salts or optical isomers thereof, the weight ratio of the EDDS and/or salts or optical isomers thereof: IDS and/or salts or optical isomers thereof is in the range of from about 20:1 up to about 1:20, more preferably from about 4:1 up to about 1:4. When the novel composition of my invention also contains indolebutyricacid ('IBA') the mole ratio of the IBA to the IDS and EDDS (and/or salts or optical isomers thereof) varies from about $5 \times 10^{-4}$:1 up to about $10 \times 10^{-4}$:1.

When the nitrogen-containing organic compounds of our invention are used to stimulate or regulate the growth of germinating plant seeds, the preferable effective weight ratio of nitrogen-containing organic compound: germinating seed is in the range of from about $6 \times 10^{-4}$:1 up to about 0.04:1. In addition, the range of effective concentrations of nitrogen-containing compound in aqueous solution is a function of the particular germinating seed being treated and whether the growth of the germinating seed is to be regulated or stimulated.

Thus, for example, when the growth of germinating sweet corn (Zea L. var.*caccharata* Sturt.) seed is to be stimulated by IDS free acid and/or EDDS free acid (the structures of which are set forth in FIGS. 11 and 12, described infra), the concentration range of IDS and/or EDDS is from about $5 \times 10^{-4}$ up to about $10 \times 10^{-4}$ gram moles per liter of treating solution, preferably in the range of from about $7 \times 10^{-4}$ up to about $8 \times 10^{-4}$ gram moles per liter.

However, surprisingly, the germinating-seed stimulating concentration of the tri-potassium salt of IDS (the structure of which is set forth in FIG. 17, infra), or the tetra-sodium salt of EDDS (the structure of which is set forth in FIG. 15, infra) is about $1 \times 10^{-4}$ gram moles per liter.

At a concentration of about $10 \times 10^{-4}$ gram moles per liter, the tetra-sodium salt of EDDS acts as a germinating seed growth regulator, however. Also, surprisingly (as will be observed from the results of Example IV, infra) the novel compositions of matter of our invention containing mixtures of IDS and EDDS free acids at concentration levels of >200 ppm (that is, greater than $7 \times 10^{-4}$ gram moles per liter) regulate the growth (by means of reduction of the rate of growth) of *Petunia violacea* Lindl. (Petunia).

Herein, the term 'growth regulator' is intended to be used to explain changes in the plant physiology whereby the rate of growth in the plants is significantly changed. Plant growth regulators are used, inter alia, for initiating growth, controlling growth, promoting flowering, thinning flowers, providing drought protection and ripening fruit.

IDS and EDDS free acids have such an effect on plant seedlings and plants. When a dose of EDDS free acid (or salts or optical isomers thereof) in combination with IDS free acid (or salts or optical isomers thereof) is applied to a germinating seed at a concentration level >200 ppm (that is, greater than $7 \times 10^{-4}$ moles per liter), germination is significantly, and surprisingly retarded. However, at concentration levels <200 ppm are applied to the same germinating seed, 'radical emergence' occurs within a significantly lower time period, and is significantly more uniform.

The practice of the immediately aforementioned aspect of my invention gives rise to a shortening of internode lengths. Bursts of vegetative growth often compete with the 'source-sink' relationships between the vegetative parts and the reproductive organs of higher plants. Those skilled in the art have often turned to Gibberelic acid transport or synthesis inhibition to control a 'flush' or 'burst' of growth, i.e., plant height. While such measures may be successful in controlling plant height, they do not normally contribute to plant 'yield'.

Uniform seedling emergence is important while preparing to harvest. Late seedling emergence may delay harvest or spread harvesting over an extended period of time. Accordingly, uniform seedling emergence and uniform growth substantially insure uniform pollination, uniform fruit setting and uniform ripening.

The aqueous nitrogen compound-containing solutions useful in the practice of my invention can be applied to plants or plant precursor as stated supra. The application may be by means of spraying on plant leaves ('foliar application'); and/or by adding in a carefully controlled manner the solution to soil in the proximity of germinating seeds or plant seedlings (e.g., from about >0 up to about 100 mm. distant from the edge of the germinating seed or plant seedling); and/or by seed priming or imbibing germinating seeds with the aqueous solution. When carrying out spraying, the spraying may be effected using any conventional means for spraying liquids such spray nozzles, atomizers, or the like.

The temperature of the aqueous solution can be controlled by means of carrying out temperature control and the admixing of the water with the nitrogen-containing compound, e.g., EDDS and/or IDS alkali metal salts, if the application step is to occur immediately subsequent to such admixture step. Otherwise, the temperature of the aqueous treatment solution is adjusted by subsequent heating or cooling, followed by storage in insulated containers as desired.

The amount and concentration of adjuvant used is a function of the particular plant or germinating plant seed treated as well as the soil composition and temperature and humidity conditions proximate the plant or germinating seed being treated.

BRIEF DESCRIPTION OF THE DRAWINGS

The teachings of the present invention can be readily understood by considering the following detailed description in conjunction with the accompanying drawings in which:

In FIGS. 1–6, inclusive, to facilitate understanding, identical reference numerals have been used, where possible, to designate identical elements that are common to the figures.

DETAILED DESCRIPTION

Figure 1:
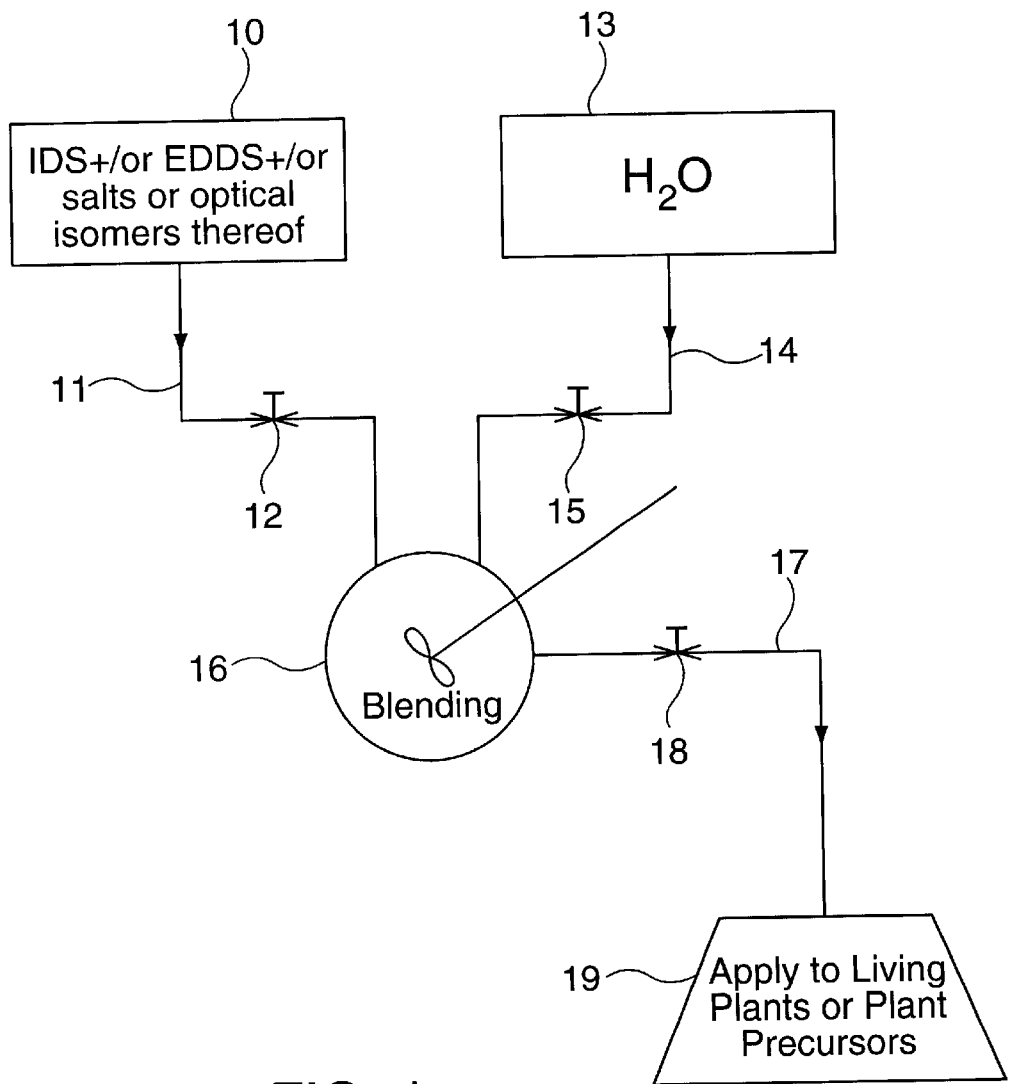
FIG. 1 sets forth a block-flow schematic diagram of an embodiment of the process of our invention, without inclusion of additional adjuvants in the aqueous solution of the nitrogen-containing compound of our invention.
Figure 4:
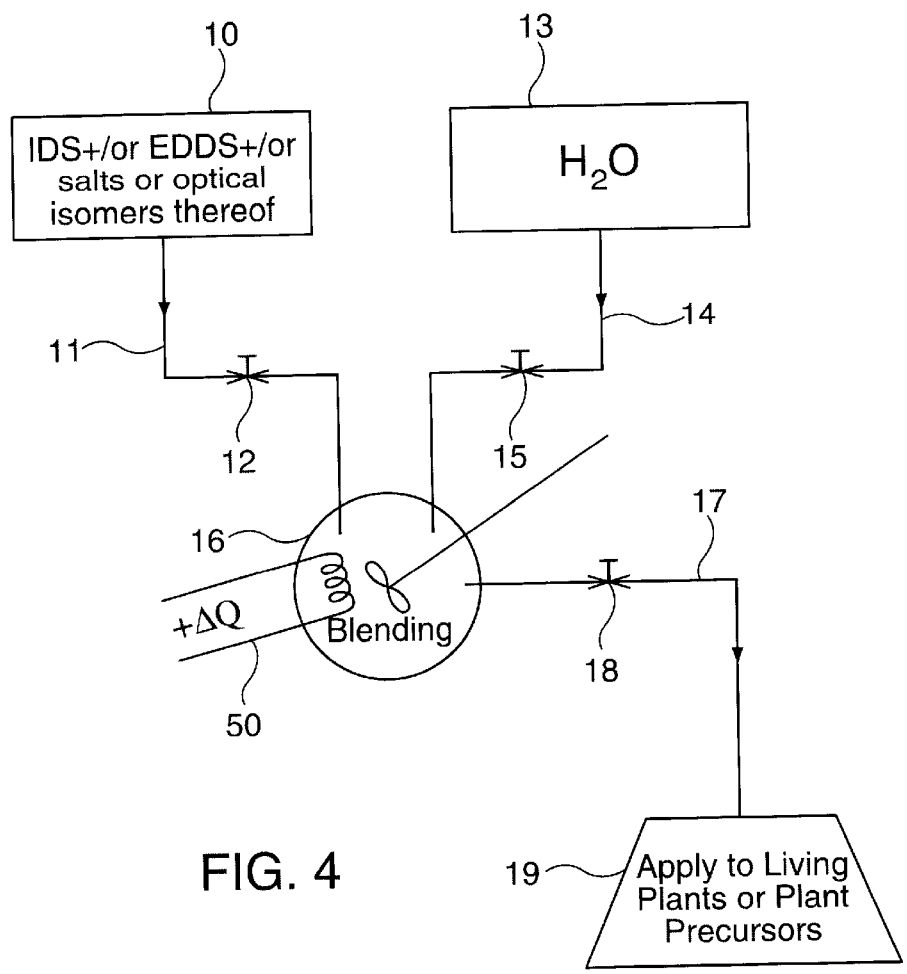
FIG. 4 sets forth a block flow diagram of the embodiment of the process of my invention of FIG. 1 with the inclusion of a heat and temperature control means in the mixing means for admixing the water with the nitrogen-containing compound(s) of our invention.

Referring to FIGS. 1 and 4, IDS and/or EDDS and/or its ammonium, alkali metal and/or its ammonium salts or optical isomers thereof (one or more of the 'nitrogen-containing compounds of my invention') at location 10 is transported through line 11 past control valve 12 into mixing vessel 16 where it is admixed, with water from location 13. The water from location 13 is transported to vessel 16 through line 14 past control valve 15. The blending may take place using temperature/heat transfer control means, shown by reference numeral 50 in FIG. 4.

The resulting aqueous solution in then transported through line 17 past control valve 18 into application means 19 (e.g., a holding vessel/spraying nozzle) from which the solution is applied to a plant precursor or plant is indicated, supra.

Figure 2:
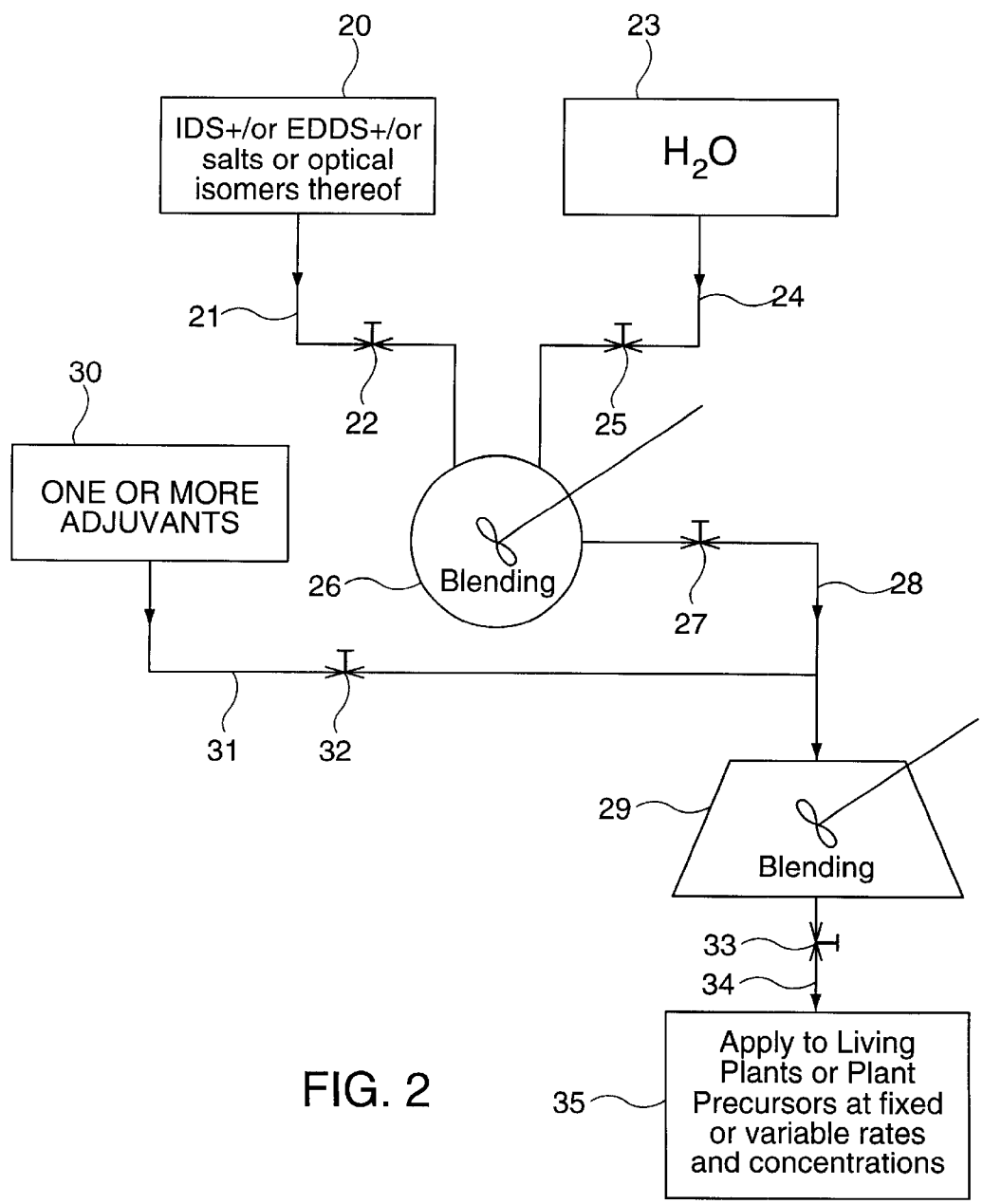
FIG. 2 sets forth a block flow diagram of a second embodiment of the process of our invention with the inclusion of the step of adjuvant addition to the pre-mixed water/nitrogen-containing compound solution prior to plant or plant precursor treatment with the resulting aqueous adjuvant-containing mixture.
Figure 5:
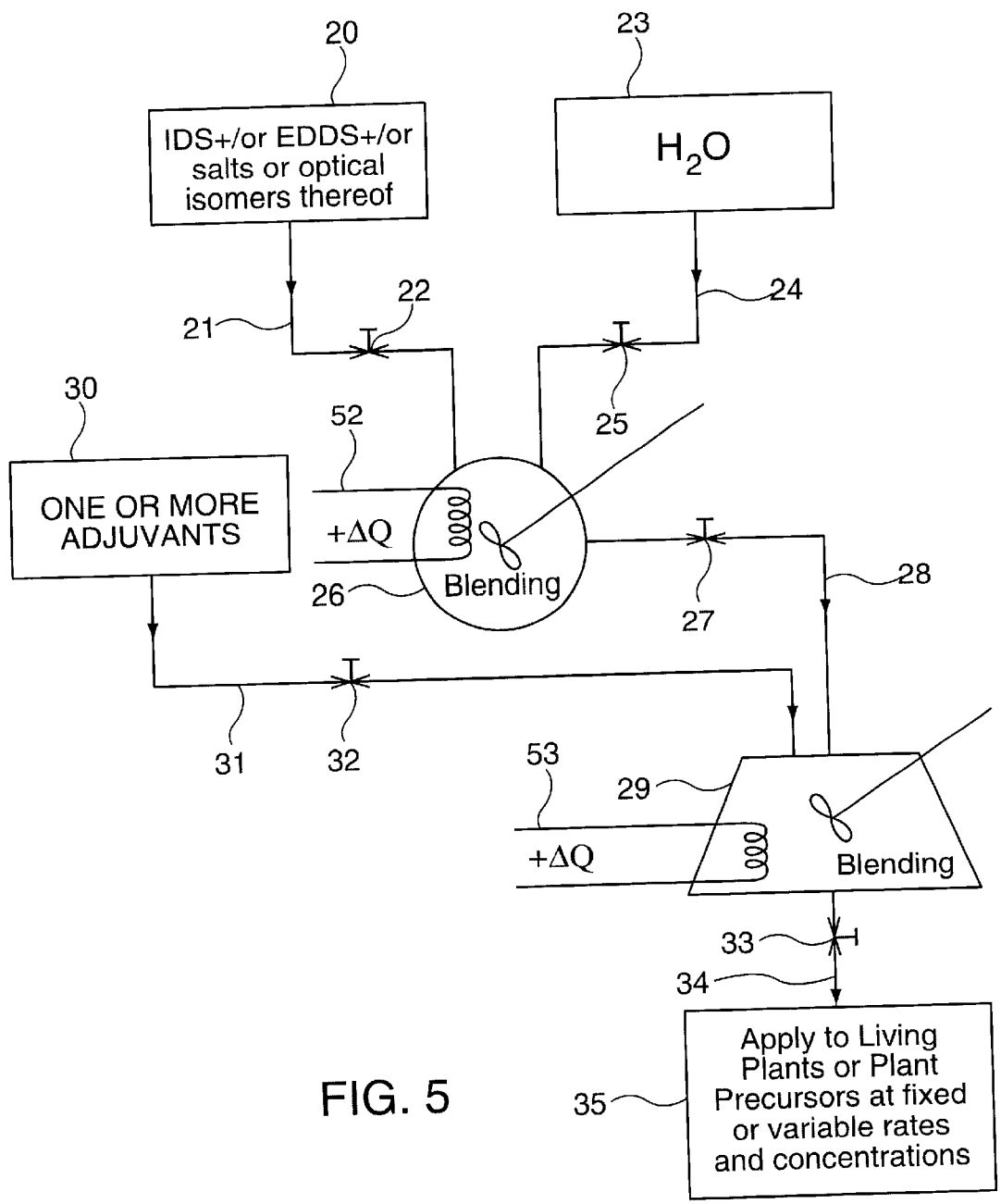
FIG. 5 sets forth a block flow diagram of the embodiment of the process of my invention of FIG. 2 with the inclusion of heat and temperature control means in (a) the mixing means for admixing the water with the nitrogen-containing compound(s) of our invention for the purpose of forming an aqueous solution; and (b) the mixing means for admixing the resulting aqueous solution with one or more adjuvants.

Referring to FIGS. 2 and 5 IDS and/or EDDS and or salts thereof or optical isomers thereof stored in vessel 20 is(are) transported via line 21 past control valve 22 into mixing vessel 26 where the compound(s) are admixed with water being transported from holding tank 23 through line 24 past control valve 25. The resulting aqueous solution may be subjected to temperature control by means of temperature control/heat transfer device 52 (shown in FIG. 5) operating in mixing vessel 26.

The resulting aqueous solution is then transported via line 28 past control valve 27 into mixing vessel 29 where the aqueous nitrogen-containing compound(s) used in the practice of my invention is blended with one or more adjuvants (as described in detail, infra) previously held in holding vessel 30 and transported to mixing vessel 29 via line 31 past control valve 32. As shown in FIG. 5, mixing vessel 29 may be equipped with heat transfer/temperature control means 53 for temperature adjustment of the resulting mixture and/or to facilitate blending and/or dissolution of the ingredients. The resulting mixture of water, nitrogen-containing compound(s) and one or more adjuvants is transported to plant or plant precursor application means 35 (e.g., holding tank/spray nozzle means) via line 34 past control valve 33 where the mixture is applied to plants or plant precursors (e.g., germinating plant seeds) as described, supra.

Figure 3:
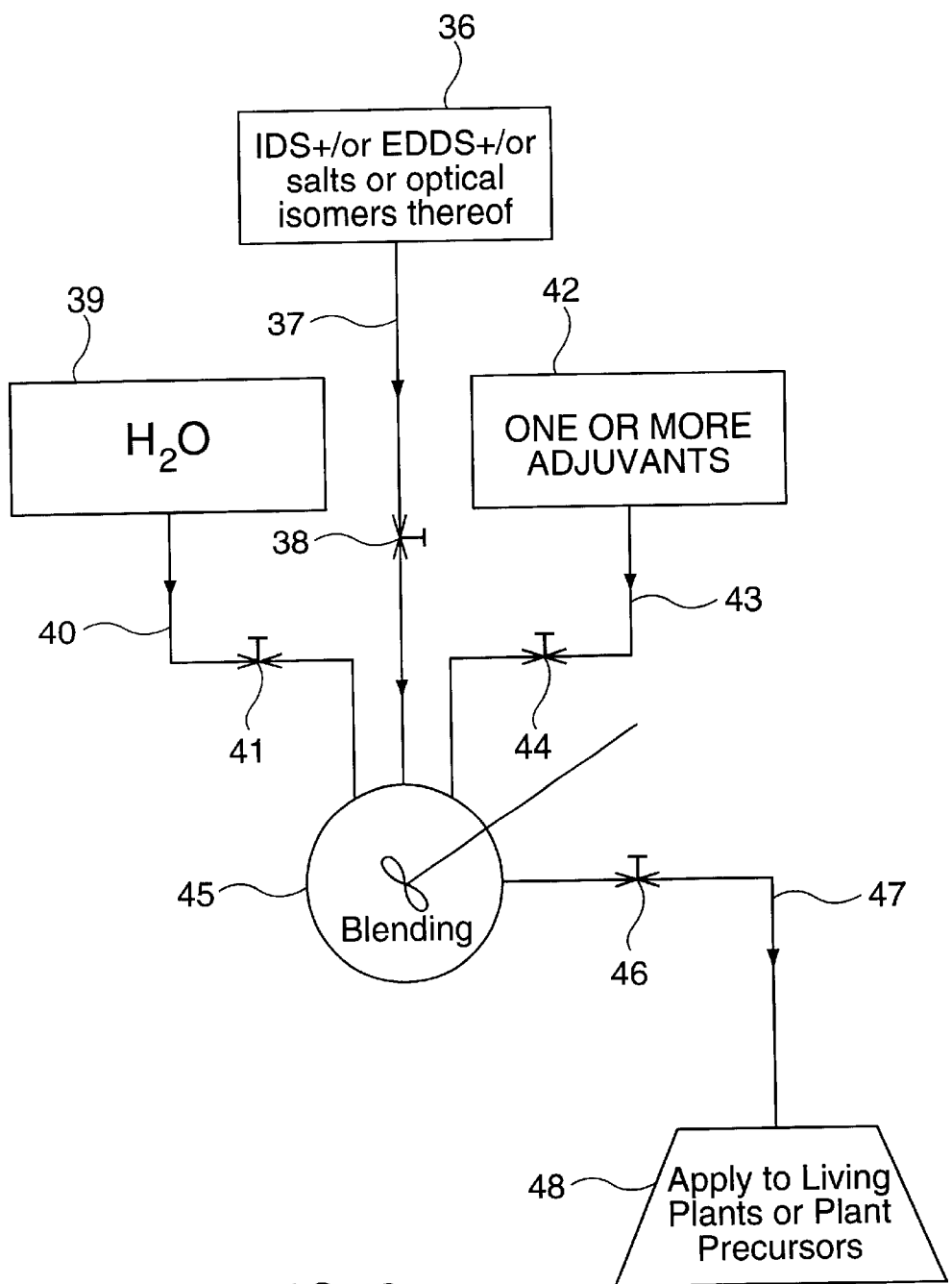
FIG. 3 sets forth a block flow diagram of a third embodiment of the process of our invention with the inclusion of the step of adjuvant addition simultaneously with the mixing of the water and nitrogen-containing compound of my invention prior to plant or plant precursor treatment with the resulting aqueous adjuvant-containing mixture.
Figure 6:
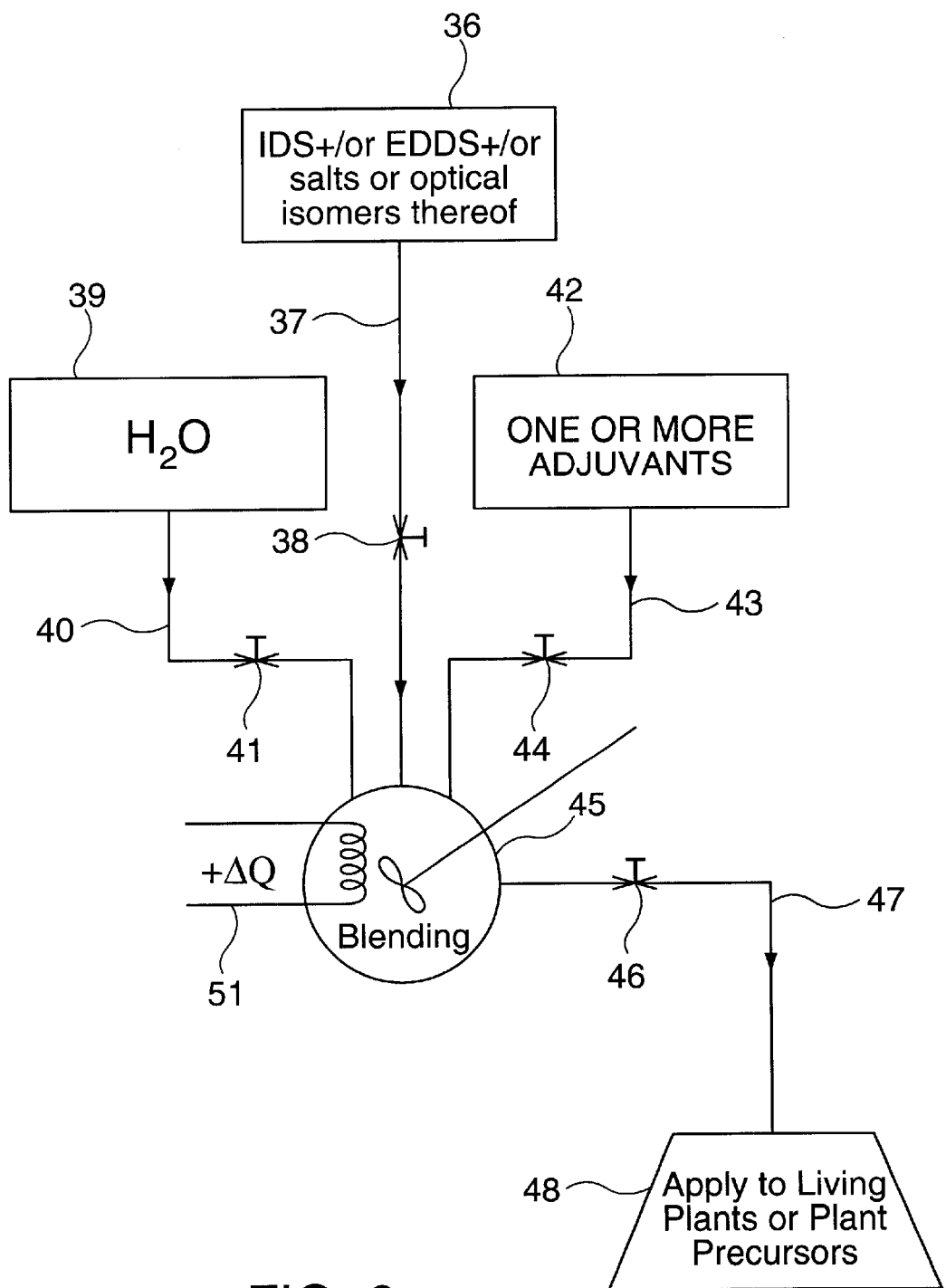
FIG. 6 sets forth a block flow diagram of the embodiment of the process of my invention with the inclusion of heat and temperature control means for admixing the water, nitrogen-containing compound of my invention, and the adjuvant(s) useful in the practice of my invention, prior to application of the resulting mixture to plant precursors or plants.
Figure 7:
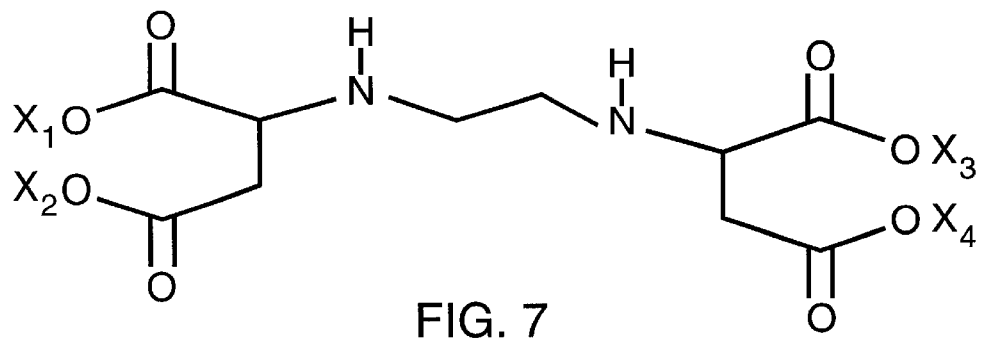
FIG. 7 sets forth a generic chemical structure for EDDS and its salts useful in the practice of my invention wherein $X_1$, $X_2$, $X_3$ and $X_4$ are the same or different hydrogen, ammonium or alkali metal.
Figure 8:
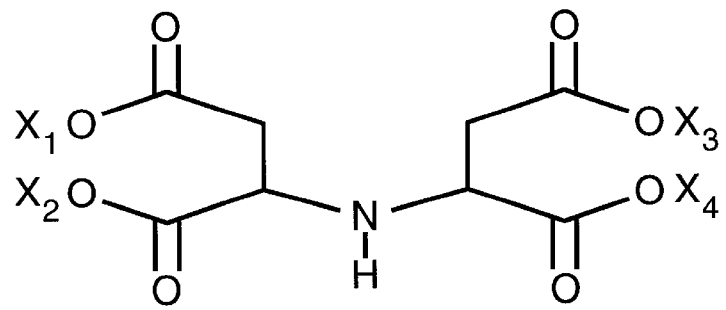
FIG. 8 sets forth a generic chemical structure for IDS and its salts useful in the practice of my invention wherein $X_1$, $X_2$, $X_3$ and $X_4$ are each the same or different hydrogen, ammonium or alkali metal.
Figure 9:
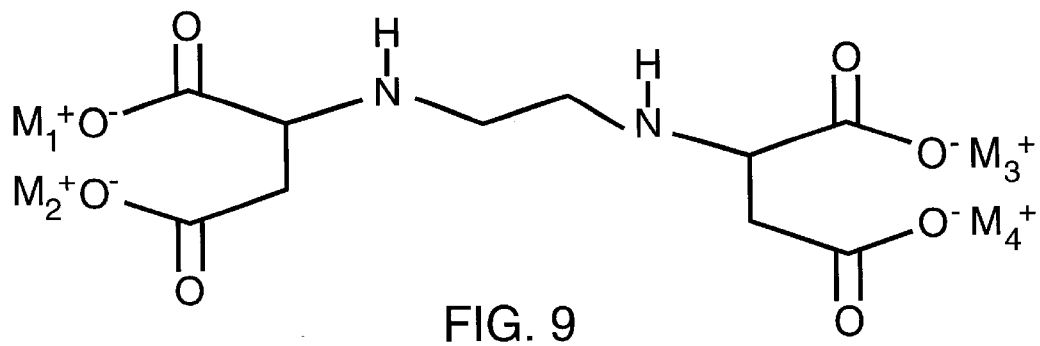
FIGS. 9 and 10, respectively set forth generic chemical structures for EDDS and IDS salts useful in the practice of our invention wherein $M_1^+$, $M_2^+$, $M_3^+$ and $M_4^+$ are each the same or different and each represents ammonium or alkali metal.
Figure 10:
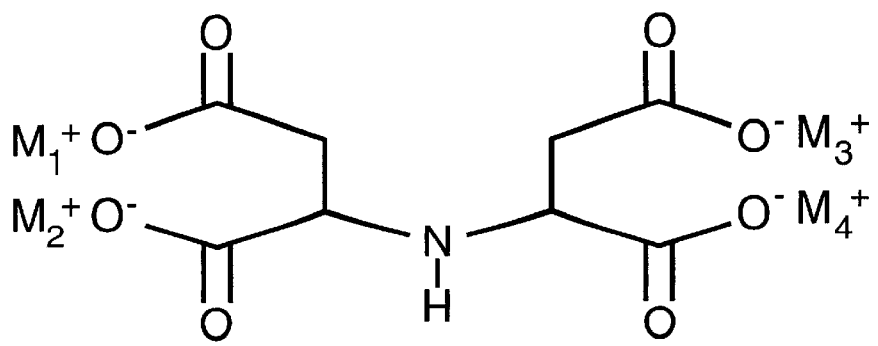

Referring to FIGS. 3 and 6, EDDS and/or IDS and/or salts thereof or optical isomers thereof, located in holding vessel 36 are passed through line 37 past control valve 38 into blending vessel 45. Simultaneously, or immediately subsequent, water from holding vessel 39 is transported to mixing vessel 45 via line 40 past control valve 41. Simultaneously, or subsequently, one or more adjuvants (as described in detail, infra) is transported into mixing vessel 45 via line 43 past control valve 44. The adjuvant(s), water and nitrogen-containing compound(s) are admixed in vessel 45 to form a solution or emulsion. Vessel 45 may optionally be equipped with a heat transfer/temperature control device 51 (as shown in FIG. 6) in order to adjust the temperature of the adjuvant-nitrogen-containing compound-water mixture and/or in order to facilitate the blending or mixing unit operation.

The resulting mixture or blend is then transported via line 47 past control valve 46 to plant or plant precursor application means 48 (e.g., holding vessel/spray nozzle means) from whence the resulting mixture is applied to plants and/or plant precursors (e.g., germinating seeds) as described, supra.

The compositions useful in the practice of my invention may be formulated in a wide range of forms known to those skilled in the art. The compositions useful in the practice of my invention may, for example, be in the form of a concentrate to be diluted prior to application, or it may be in the form of a granule, powder or liquid with a suitable solid or liquid carrier. Thus, for example, compositions useful in the practice of my invention may be in the form of emulsions, or aqueous dispersions, and may include solvents. In the alternative, the compositions useful in the practice of my invention may be adapted to form an emulsion prior to use.

Operating concentrations higher than those set forth supra of the EDDS (or salts thereof or optical isomers thereof) and/or IDS (or salts thereof or optical isomers thereof)- containing formulations useful in the practice of our invention may be used when, for example, the application to the plant or plant precursor of such compositions is in a form suitable for use as an ultra-low volume spray which merely contains the active nitrogen-containing compounds of my invention, e.g., the IDS (or salts or optical isomers thereof) and/or the EDDS (or salts or optical isomers thereof).

The compositions useful in the practice of my invention can be prepared in the form of wettable powders, soluble powders, dusting powders, granulates, solutions, emulsifiable concentrates emulsions (as stated supra), suspended concentrates or aerosols, or in microencapsulated form (produced, for example, via coacervation) for controlled release application to pants or plant precursors of the active nitrogen-containing compound components, e.g., the IDS and/or EDDS free acids and/or salts thereof or optical isomers thereof.

The wettable powders useful in the practice of my invention can be prepared in such a manner that they contain the active nitrogen-containing compound; and such wettable powders normally contain, in addition to a solid support, a wetting agent, a dispersant, and, when appropriate, one or more stabilizers and/or other additives such as penetration agents, adhesives, colorants, or anti-lumping agents.

Aqueous dispersions and emulsions, such as, for example, compositions obtained by diluting with water a wettable powder or an emulsifiable concentrate are intended to be included within the general scope of my invention. Such emulsions may be of the 'water-in-oil' type or of the 'oil-in-water' type and may have the consistence resembling that of a 'mayonnaise'.

As stated supra, the step of the process of my invention, of formulating the aqueous plant precursor or plant growth-regulating or stimulating solution may also (optionally) include (prior to the step of application to the plant precursor or plant or proximity thereof) the simultaneous admixing or the immediately-subsequent admixing of the aqueous nitrogen-containing compound solution with at least one adjuvant selected from the group consisting of:

(a) carriers;

(b) surfactants;

(c) carbon skeleton energy adjuvants;

(d) vitamin/co-factor adjuvants;

(e) gums;

(f) anti-microbial agents;

(g) buffers;

(h) protective colloids;

(i) viscosity modifiers; and (j) growth regulators

Examples of which are as follows:

(a) Carriers

In the context of my invention, a carrier is an organic or inorganic natural or synthetic material with which the active material is associated to facilitate its application to the plant, to the seeds, or to the soil proximate to said seed and/or plant, or its transportation or handling. The support can be a solid (e.g., clays, natural or synthetic silicates, resins and waxes) or fluid (e.g., water, alcohols, ketones, petroleum fractions, chlorinated hydrocarbons and liquified gases).

(b) Surfactants

The compositions useful in the practice of my invention may include one or more surfactants which aid in the preparation of other compositions and which may assist in the penetration of active components through plant or seed membranes. Such surfactants include anionic, cationic, nonionic and zwitterionic surfactant. Anionic surfactants include alkyl aryl ethoxylates, fatty acid ethoxylates, vegetable seed oil ethoxylates, sorbitan fatty acid ester ethoxylates, or other alkoxylates. More specifically, a useful surfactant is the compound, $C_9H_{19}$-(phenylene)-$(OCH_2CH_2)_9OH$ also known as NONOXYNOL-9™ or NP-9™. Thus, the surfactant can be an ionic or non-ionic emulsifier, dispersant or wetting agent such as, for example, salts of polyacrylic acids, condensates of ethylene oxide with fatty alcohols, fatty acids or fatty amines. Such surfactants are more specifically set forth in U.S. Pat. No. 6,184,182 issued on Feb. 6, 2001 (U.S. Class 504, subclass 116), the disclosure of which is incorporated herein by reference.

(c) Carbon Skeleton Energy Adjuvants

The function of this component is to supply one or more carbon skeletons for the synthesis of proteins and other molecules or to supply energy for metabolism. Water-soluble carbohydrates such as sucrose, fructose, glucose and other di- and monosaccharides are suitable, commonly in the form of molasses or other byproducts of food manufacture. Commercially available lignosulfonates are also suitable as a 'CSE' source, inasmuch as they commonly contain sugars. More specifically, examples of CSE sugars are: mannose, lactose, dextrose, fructose, fucose, raffinose, xylose and arabinose. Sugar alcohols are also useful CSE's, specifically, for example, maltitol, mannitol, sorbitol and xylitol. Organic acids are useful CSE's, for example, alpha-ketoglutaric acid, pyruvic acid, succinic acid, citric acid, and aspartic acid. Nucleotides are useful CSE's, for example, adenosine, uridine, thymine, cytosine, guanine and guanosine.

(d) Vitamin/co-factor Adjuvants

Examples of useful vitamin/co-factor adjuvants in the practice of my invention are folic acid, biotin, pantothenic acid, nicotinic acid, riboflavin and thiamin, as well as derivatives thereof. For example, useful thiamine derivatives are thiamine disulfide and thiamine hydrochloride. Useful riboflavin derivatives are flavin adenine dinucleotide and flavin adenine mononucleotide. Useful nicotinic acid derivatives are nicotinic acid amide, nicotinic acid benzyl ester, nicotinic acid methyl ester and nicotinic acid nitrile. A useful biotin derivative is biotin methyl ester.

(e) Gums

Examples of gums useful as adjuvants I the practice of my invention are xanthan gum, guar gum, gum arabic gum carageenan, gum elemi, locust bean gum and gum tragacanth.

(f) Anti-microbial Agents

Examples of anti-microbial agents useful in the practice of my invention are propionic acid, benzoic acid, thymol, indole, and sorbic acid.

(g) Buffers

Examples of buffers useful in the practice of my invention are alkali metal (sodium or potassium) formates, carbonates, bicarbonates, propionates, benzoates and/or acetates.

(h) Protective Colloids

Examples of agents which form protective colloids surrounding and/or emicro-encapsulating the nitrogen-containing active compounds useful in the practice of my invention are gelatin, colloidal silica and colloidal alumina. In addition, the gums cited supra when appropriately applied have the ability to form such protective colloids.

(i) Viscosity Modifiers

Examples of viscosity modifiers useful in the practice of my invention are terpenes, such as myrcene, dihydromyrcene, terpene derivatives such as citronellol, and those materials set forth in U.S. Pat. No. 5,447,644, the disclosure of which is incorporated herein by reference.

(j) Growth Regulators Seaweed extract—kelp extract, Kinetin, Kinetin riboside, benzyladenine, zeatin riboside, zeatin, extract of corn cockle, isopentenyl adenine, dihydrozeatin, indoleacetic acid, phenylacetic acid, IBA, indole ethanol, indole acetaldehyde, indoleacetonitrile, indole derivitives, gibberellins (e.g., GA1, GA2, GA3, GA4, GA7, GA38, etc.) polyamines, monoethanolamine, allopurinol, GA inhibitors, ethylene inducing compounds, ethylene biosynthesis inhibitors, GABA, anticytokinins and antiauxins, ABA inducers and inhibitors, and other known growth regulators.

The following examples are illustrative, and my invention is only limited by the scope of the claims following the examples.

EXAMPLE I

Title: Use of the Tetra-sodium Salt of EDDS on Germinating Sweet Corn Field Corn, Cantaloupe Melon and Snap Bean Seeds Styrofoam plates were each charged with 80 ml. water. The plates are titled: (a) the 'control' plates; (b) the 'Treatment 1' plates; and (c) the 'Treatment 2' plates.

Into the 'control' plates, the 'Treatment 1' plates and the 'Treatment 2' plates were placed, at the loading of 10 seeds per plate, germinated sweet corn seeds, germinated field corn seeds, germinated snap bean, seeds, germinated cantaloupe melon seeds and germinated soy bean seeds.

Figure 15:
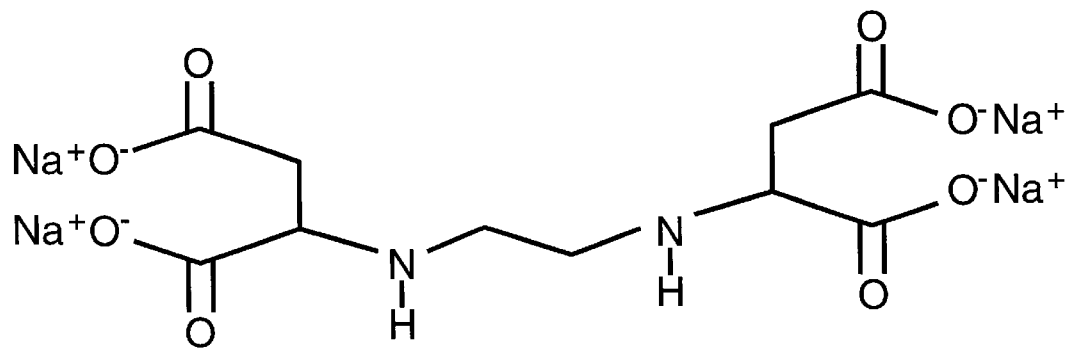
FIG. 15 sets forth the chemical structure of the tetra-sodium salt of EDDS.
Figure 16:
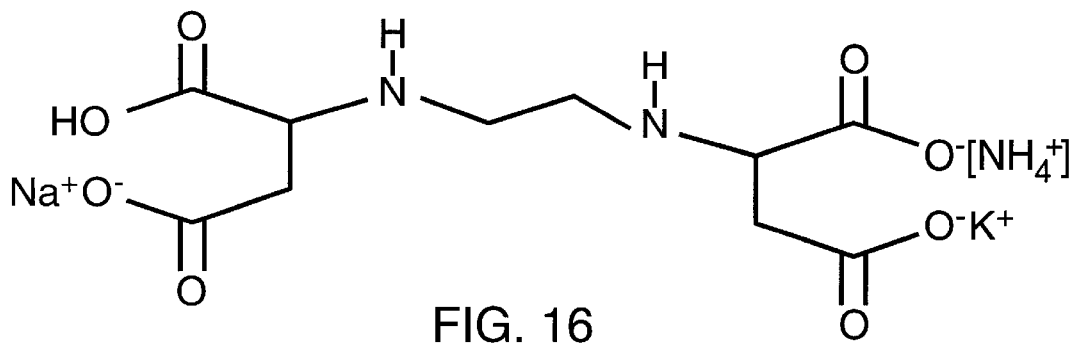
FIGS. 16 and 19 set forth, respectively, the chemical structures of the sodium-potassium-$NH_4^+$ salts of EDDS and IDS.

The 'Treatment 1' plates were then each treated with 0.1 ml. of a 38% aqueous solution of the tetra-sodium salt of EDDS (having the structure as set forth in FIG. 15), or 0.000475 gm./plate, or 475 ppm per plate.

The 'Treatment 2' plates were then each treated with 1 ml. of a 38% aqueous solution of the tetra-odium salt of EDDS, or 0.00475 gm./plate or 4750 ppm per plate.

No EDDS salt was added to the 'control' plate.

Over a period of 9 days, each plate had distilled water added thereto, as needed, in order to make up for the evaporation of the water during the 9 day period.

9 days after the trial commenced, the number of germinated seeds which survived were as set forth in attached Table I.

The soy bean test was void, since mold had developed on the soy beans and no seed were viable.

The 'Treatment 1' plates, after 9 days, showed uniform germination and growth of the germinated sweet corn seeds, as compared with the control.

The 'Treatment 2' plates, after 9 days, showed inhibition of the germination and growth of the sweet corn.

The 'Treatment 2' plates, after 9 days, showed inhibition of the germination and growth of the field corn.

EXAMPLE II

Title: Use of the Tri-potassium Salt of IDS, Alone, or Toegether with the Tetra-potassium Salt of EDDS on Germinating Seet Corn, Field Corn and Cantaloupe Melon Seeds Styrofoam plates were each charged with 80 ml. water. The plates are titled: (a) the 'control' plates; (b) the 'Treatment 1' plates; (c) the 'Treatment 2' plates and (d) the 'Treatment 3' plates.

Into the 'control' plates, the 'Treatment 1' plates, the 'Treatment 2' plates and the 'Treatment 3' plates, were placed, at a loading of 6 seeds per plate, sweet corn seeds, field corn seeds, cantaloupe melon seeds and soy bean seeds.

Figure 17:
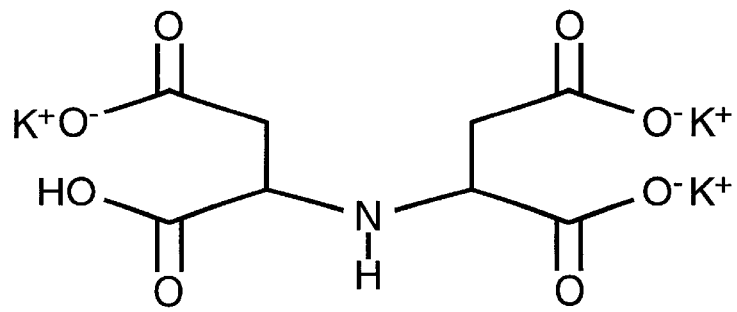
FIG. 17 sets forth the chemical structure of the tri-potassium salt of IDS.

The 'Treatment 1' plates were then each treated with 1 ml. of a 37% solution of the tri-potassium salt of IDS (having the structure as set forth in FIG. 17), or 0.00463 gm./plate or 4630 ppm per plate.

The 'Treatment 2' plates were then each treated with 0.1 ml. of a 37% solution of the tri-potassium salt of IDS, or 0.000463 gm./plate, or 463 ppm per plate.

The 'Treatment 3' plates were then each treated with a mixture 0.5 ml. of a 37% solution of the tri-potassium salt of IDS and 0.5 ml. of a 38% solution of the tetra-sodium salt of EDDS, or 0.000231 gm/plate of the IDS salt and 0.000238 gm./plate of the EDDS salt.

No EDDS or IDS salts were added to the control plate.

Over a period of 9 days, each plate had distilled water added thereto, as needed, in order to make up for the evaporation of water during the 9 day period.

9 days after the trial commenced, the number of germinated seeds which survived were as set forth in attached Table II.

The sweet corn seeds treated with the IDS salt and the combination of the IDS and EDDS salts germinated and the resulting seedlings started to grow more uniformly.

The field corn seeds treated with the mixture of the IDS and EDDS salts commenced germinating during the 9 days period, and commenced growing more uniformly during the nine day period.

EXAMPLE III

Figure 18:
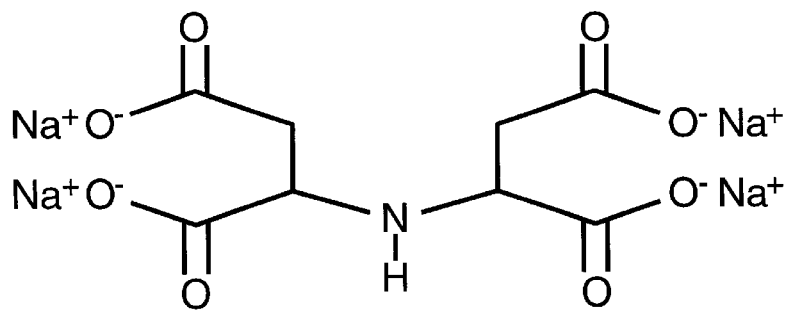
FIG. 18 sets forth the chemical structure of the tetra-sodium salt of IDS.
Figure 19:
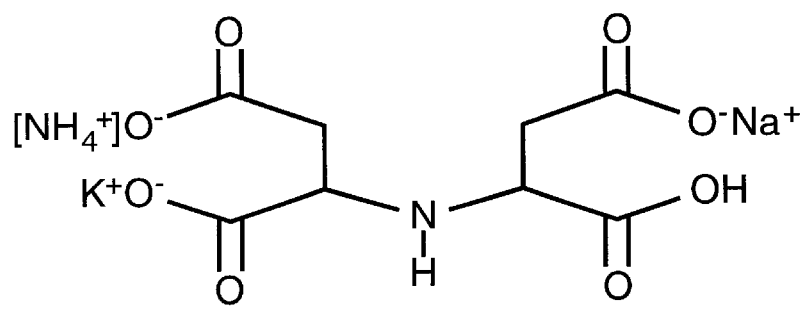
Figure 20:
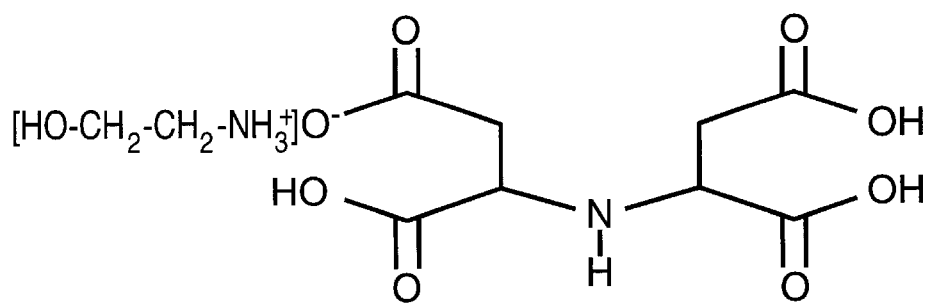
FIGS. 20 and 21 set forth, respectively, the chemical structures of the mono-2-hydroxyethylammonium salts of IDS and EDDS.
Figure 21:
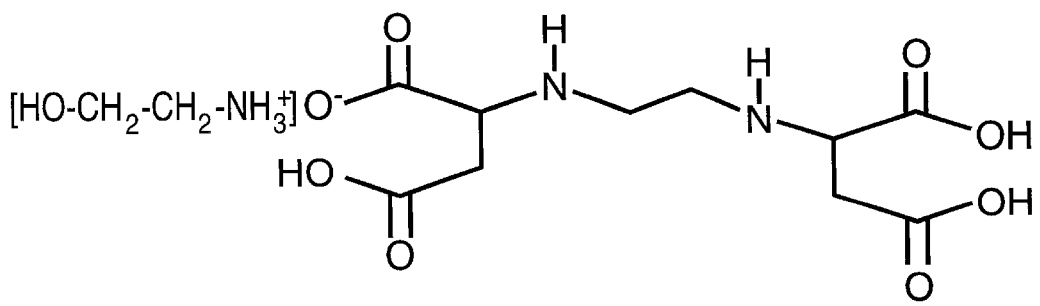
Figure 22:
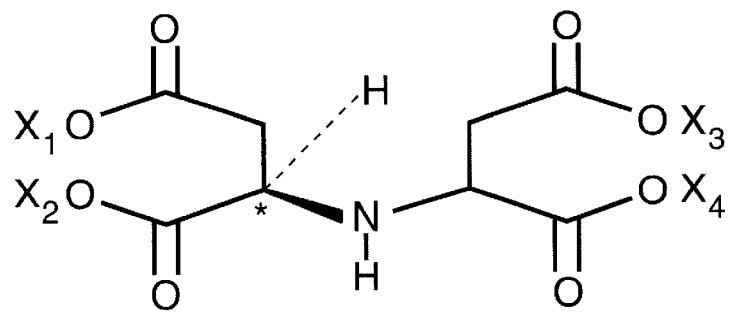
FIG. 22 sets forth a representation of a generic stereoisomer structure of IDS wherein the "(*)" indicates the location of an asymmetric carbon atom and wherein each of $X_1$, $X_2$, $X_3$ and $X_4$ represents the same or different hydrogen, ammonium or alkali metal.
Figure 23:
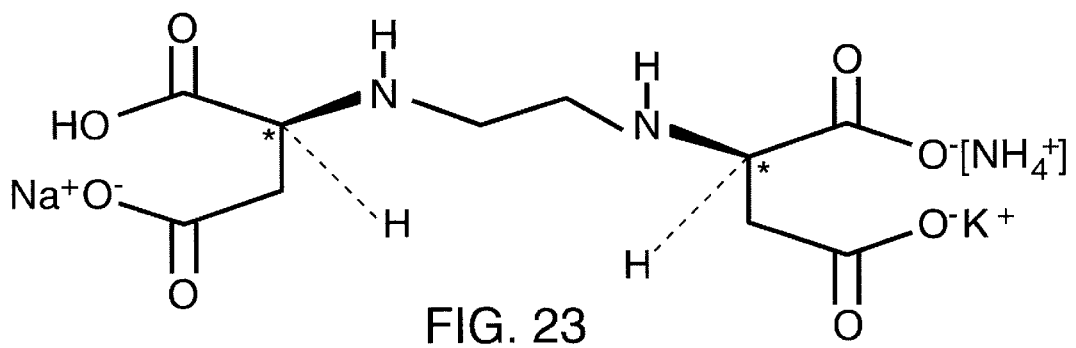
FIG. 23 sets forth a stereoisomer of the EDDS sodium-potassium-$NH_4^+$ salt, useful in the practice of my invention wherein each of the "(*)"'s indicates the location of an asymmetric carbon atom.
Figure 24:
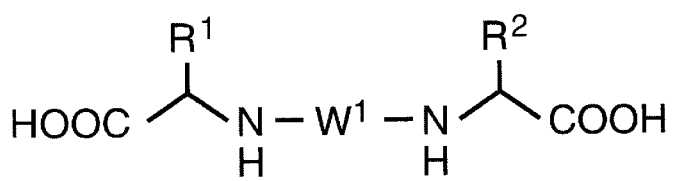
FIGS. 24 and 25 are the two generic structures set forth in the Takahashi et al Japanese Kokai No. 11-29415 and are fully described herein in the 'BACKGROUND OF THE DISCLOSURE/Description of the Prior Art' section of this specification, supra.
Figure 25:
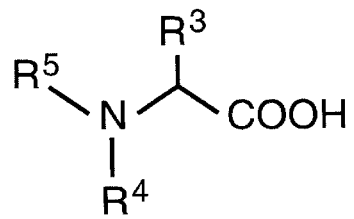

Title: Use of the EDDS Free Acid and/or the IDS Free Acid on Germinating Field Corn Seeds 100 ml. each of 37% solutions of the tetra-sodium salt of IDS having the structure as set forth in FIG. 18 and the tetra-sodium salt of EDDS having the structure as set forth in FIG. 15 were placed in beakers and sufficient 29% aqueous HCl was added thereto to complete the formation of IDS and EDDS free acid crystals.

0.2 grams/liter of each of the free acids was added to distilled water to yield 1 liter stock solutions of each free acid, at a concentration of 0.2 gm/liter.

Seven styrofoam plates were provided, titled: (a) the 'control' plate; (b) the 'Treatment A' plate; (c) the Treatment B' plate; (d) the 'Treatment C' plate; (e) the 'Treatment D' plate and (f) the 'Treatment E' plate.

To each plate, eight (8) field corn seeds were added.

To the 'control' plate, 100 ml. of distilled water was added.

To the 'Treatment A' plate, 100 ml. of EDDS stock solution was added (200 ppm EDDS).

To the 'Treatment B' plate, 20 ml. of IDS stock solution and 80 ml. of EDDS stock solution was added (40 ppm IDS and 160 ppm EDDS).

To the 'Treatment C' plate, 40 ml. of IDS stock solution and 60 ml. of EDDS stock solution was added (80 ppm IDS and 120 ppm EDDS).

To the 'Treatment D' plate, 60 ml. of IDS stock solution and 40 ml. of EDDS stock solution was added (120 ppm IDS and 80 ppm EDDS).

To the 'Treatment E' plate, 80 ml. of IDS stock solution and 20 ml. of EDDS stock solution was added (160 ppm IDS and 40 ppm EDDS).

To the 'Treatment F' plate, 100 ml. of IDS stock solution was added (200 ppm IDS).

The treatments are tabulated in attached Table III.

When the corn seeds were subject to Treatment B, C, D and E, both growth rates and germination rates of the field corn seed and resultant seedlings increased significantly.

The combinations of the IDS and EDDS free acids in proportions (by weight) of from 4:1 up to 1:4 have merit for growth stimulation.

From the results of this example, one having ordinary skill in the art will conclude that concentrations of IDS and EDDS free acids greater than 200 ppm will significantly slow, delay and inhibit the growth of field corn seedlings.

EXAMPLE IV

Title: Effect of IDS and/or EDDS Free Acids on Mexican Heather

Four sets of six Mexican Heather plants each were placed on trays without transplanting. 0.2 gm/liter stock solutions of IDS and EDDS free acids prepared according to Example III, supra, were used, in three different treatments (EDDS alone, IDS alone and a 50:50 mixture of EDDS and IDS) to treat the three sets of plants as set forth in Table IV, attached, by placing the solutions into the soil within 10 mm. of each of the plants. A fourth set was treated with distilled water (the 'control' set).

Soil application of EDDS to Mexican heather promoted a greater root mass at the expense of vegetative growth. At the end of the experiment, the plant leaves are lower on the main stem and internode lengths are shortened.

Soil application of IDS to Mexican heather promoted a greater root mass at the expense of vegetative growth, although to a significantly lesser extent than done using EDDS.

EXAMPLE V

Title: Effect of IDS/EDDS Free Acid Mixture on Petunia

Three sets of six Petunia plants were placed on trays without transplanting. Two sets of plants. 'Treatment set 1' and 'Treatment set 2' were each treated with a mixture of 50 ml. IDS free acid stock solution and 50 ml. EDDS free acid stock solution, prepared according to Example III, supra. The treatments were effected by placing solutions into the soil within a 10 mm. distance from the roots of each of the plants.

Figure 26:
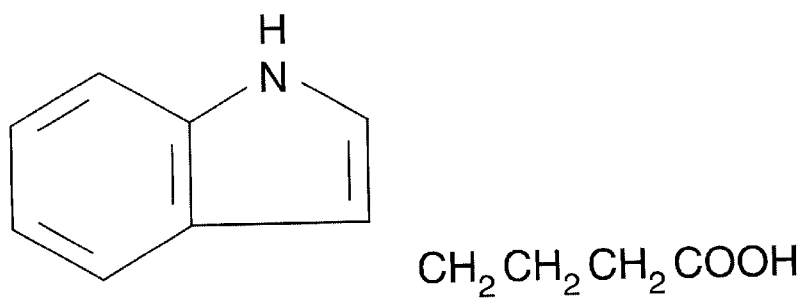
FIG. 26 (located immediately after FIG. 4) sets forth the structure of indolebutyric acid ('IBA').

The 'Treatment set 2' test solution also contained 0.001 gm./liter of indolebutyric acid having a structure as set forth in FIG. 26, in admixture with a surfactant which is a nona-ethoxylated nonyl phenol, NONOXYNOL-9™ having the structure: $C_9H_{19}$-(phenylene)-$(OCH_2CH_2)_9OH$.

A third set was treated solely with distilled water (the 'control' set).

The treatments are summarized in the attached Table V, with the 'Treatment set 2' being marked with an '*' to indicated use of the 'IBA' in that particular treatment.

Figure 11:
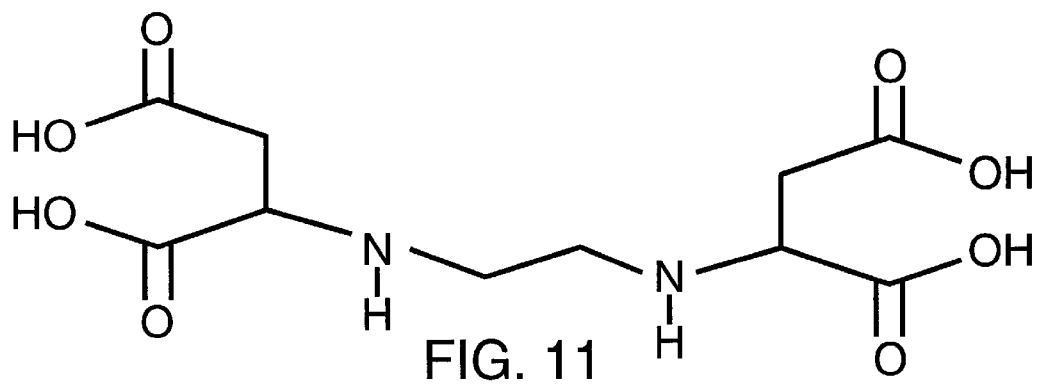
FIG. 11 sets forth the structure for EDDS free acid.
Figure 12:
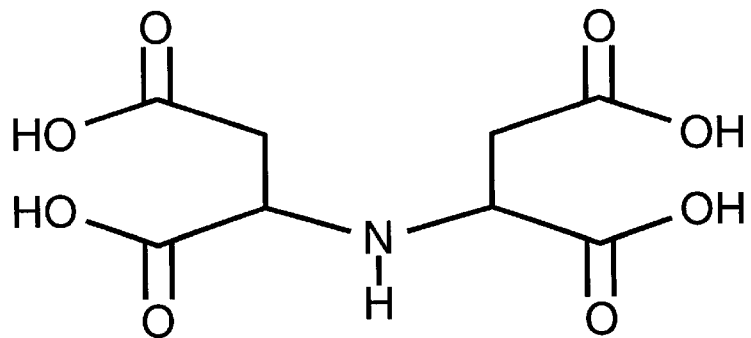
FIG. 12 sets forth the structure for IDS free acid.
Figure 13:
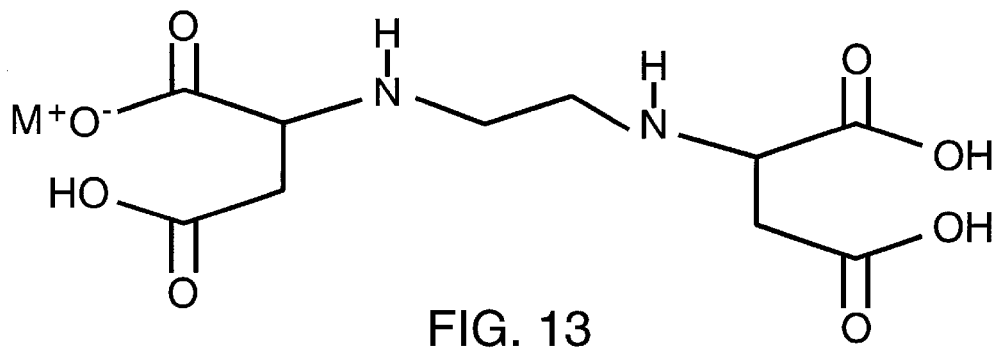
FIGS. 13 and 14 set forth, respectively the structures for mono-ammonium or mono-alkali metal salts of EDDS and IDS, wherein $M^+$ is alkali metal or ammonium.
Figure 14:
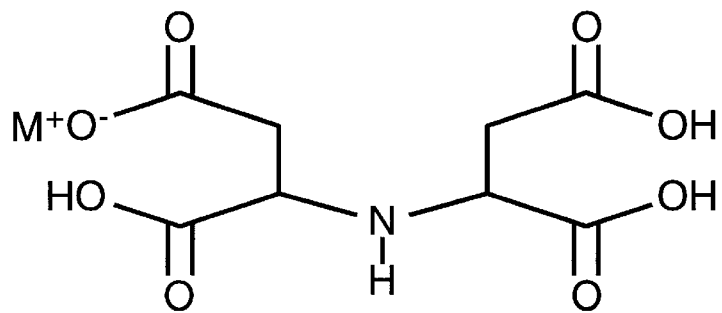

Combinations of EDDS and IDS free acids (having, respectively, the chemical structures set forth in FIGS. 11 and 12), at 200 ppm ($7 \times 10^{-4}$ moles per liter) slowed the growth of the Petunia plant. The plants treated with the IDS-EDDS free acid combination are more compact with shorter internodes; and have a significantly lower mass.

In addition, when the 'IBA' is used in conjunction with the EDDS-IDS mixture, the plants are 'stunted'.

Although various embodiments which incorporate the teachings of the present invention have been shown and described in detail herein, those skilled in the art can readily devise many other varied embodiments that still incorporate these teachings.

TABLE I (EXAMPLE I)
NUMBER OF SEED GERMINATED AND SURVIVED

| Crop | Control (water) | Treatment 1 (EDDS at 0.1 ml Per liter) | Treatment 2 EDDS at 1 ml Per liter) |
| --- | --- | --- | --- |
| Sweet corn | 7 | 10 | 7 |
| Field corn | 7 | 9 | 4 |
| Snap beans | 4 | 5 | 1 |
| Cantaloupe melon | 0 | 1 | 0 |

TABLE II (EXAMPLE II)
NUMBER OF SEED GERMINATED AND SURVIVED

| Crop | Control (water) | Treatment 1 (IDS @ 1 ml Per liter) | Treatment 2 (IDS @ 0.1 ml Per liter) | Treatment 3 (IDS @ 0.5 ml per liter and EDDS @ 0.5 ml per liter) |
| --- | --- | --- | --- | --- |
| Sweet corn | 4 | 4 | 5 | 6 |
| Field corn | 2 | 2 | 2 | 4 |
| Cantaloupe melon | 1 | 1 | 1 | 1 |
| Soy bean[2] | 0 | 0 | 0 | 0 |

TABLE II (EXAMPLE III)

| Treatment | ml of 0.2 g/l IDS | ml OF 0.2 g/l EDDS | PARTS PER 1000 IDS | PARTS PER 1000 EDDS | grams of IDS per plate | grams of EDDS per plate | ppm IDS | ppm EDDS |
| --- | --- | --- | --- | --- | --- | --- | --- | --- |
| Control | 0 | 0 | 0 | 0 | 0 | 0 | 0 | 0 |
| A | 0 | 100 | 0 | 0.2 | 0 | 0.02 | 0 | 200 |
| B | 20 | 80 | 0.04 | 0.16 | 0.0008 | 0.0128 | 40 | 160 |
| C | 40 | 60 | 0.08 | 0.12 | 0.0032 | 0.0072 | 80 | 120 |
| D | 60 | 40 | 0.12 | 0.08 | 0.0072 | 0.0032 | 120 | 80 |
| E | 80 | 20 | 0.16 | 0.04 | 0.0128 | 0.0008 | 160 | 40 |
| F | 100 | 0 | 0.2 | 0 | 0.02 | 0 | 200 | 0 |

TABLE IV (EXAMPLE IV)

| | 0.2 ml/1 EDDS acid stock solution | 0.2 ML/1 of IDS acid stock solution | IDS ppm | EDDS ppm |
|---|---|---|---|---|
| Control (water) | 0 | 0 | 0 | 0 |
| Treatment 1 | 100 ml | 0 | 0 | 200 |
| Treatment 2 | 0 | 100 ml | 200 | 0 |
| Treatment 3 | 50 ml | 50 ml | 100 | 100 |

TABLE V (EXAMPLE V)

| | 0.2 ml/1 EDDS acid stock solution | 0.2 ML/1 of IDS acid stock solution | IDS ppm | EDDS ppm |
|---|---|---|---|---|
| Control (water) | 0 | 0 | 0 | 0 |
| Treatment 1 | 50 ml | 50 ml | 100 | 100 |
| Treatment 2 | 50 ml | 50 ml | 100 | 100 |

What is claimed is:

1. A fertilizer-free and Group IIa or higher Group metal cation-free composition of matter consisting essentially of water and a plant precursor or plant growth stimulating or regulating concentration of a mixture of (a) IDS and/or one or more of its ammonium salts, alkali metal salts, ammonium-alkali metal salts or optical isomers thereof; (b) EDDS and/or one or more of its ammonium salts, alkali metal salts, ammonium-alkali metal salts or optical isomers thereof ; and, optionally, 1 H-indole-3-butanoic acid, with the weight ratio of (a):(b) being from about 1:20 up to about 20:1.

2. The composition of claim 1 wherein the alkali metal salts are selected from the group consisting of sodium salts and potassium salts.

3. The composition of claim 1 wherein the weight ratio range of (a):(b) is from about 1:4 up to about 4:1.

4. The composition of claim 1 wherein the ammonium salt is selected from the group consisting of (a) $NH_4^+$ and (b) $HO-CH_2-CH_2-NH_3^+$.

5. The composition of claim 1 which also contains 1H-indole-3-butanoic acid.

6. The composition of claim 1 wherein the weight ratio of (a):(b) is about 1:1.

7. The composition of claim 6 wherein the alkali metal salts are selected from the group consisting of sodium salts and potassium salts.

8. The composition of claim 1 intimately admixed with at least one adjuvant selected from the group consisting of:
   (a) carriers;
   (b) surfactants;
   (c) carbon skeleton energy adjuvants;
   (d) vitamin/co-factor adjuvants;
   (e) gums;
   (f) anti-microbial agents;
   (g) buffers;
   (h) protective colloids; and
   (i) viscosity modifiers.

9. The composition of claim 8 which also contains 1H-indole-3-butanoic acid.

10. The composition of claim 9 wherein the mole ratio of 1H-indole-3-butanoic acid:mixture of IDS and EDDS is from about $5\times10^{-4}$:1 up to about $10\times10^{-4}$:1.

11. A process for stimulating or regulating, substantially in the absence of any fertilizer or any Periodic Table Group IIa or higher Group cations or chelated metals, the growth of a living, growing plant precursor which is-a germinating seed, or plant having a degree of maturity of from about >0% of full growth, the seedling stage, up to about <100% of full growth, the late maturity stage, consisting of the steps of:
   (a) formulating an aqueous plant precursor or plant growth-regulating or stimulating solution consisting essentially of water, substantially free of any (i) fertilizer and (ii) Periodic Table Group IIa or higher Group metal cations or chelated metals; at least one substantially pure nitrogen-containing compound selected from the group consisting of IDS, EDDS, ammonium salts thereof, alkali metal salts thereof, ammonium-alkali metal salts thereof and optical isomers thereof; and, optionally, 1H-indole-3-butanoic acid;
   (b) providing a living, growing (i) plant precursor, or (ii) plant having a degree of maturity from about >0% up to about <100% of full growth; and
   (c) applying, in the absence of any fertilizer or any Periodic Table Group IIa or higher Group metal cations or chelated metals, a plant precursor or plant growth stimulating or regulating concentration and quantity of said aqueous plant precursor or plant growth-regulating or stimulating solution to said plant precursor or to said plant or to the effective proximity of said plant precursor or said plant, over a period of time and at a rate such that the plant precursor growth or the plant growth is stimulated or regulated.

12. The process of claim 11 wherein the ammonium salt is selected from the group consisting of (a) $NH_4^+$ and (b) $HO-CH_2-CH_2-NH_3^+$.

13. The process of claim 11 wherein the formulation step (a) includes the introduction into the formulated nitrogen-containing compound solution of an adjuvant.

14. The process of claim 11 wherein the plant precursor or plant is a plant.

15. The process of claim 14 wherein the plant is *Petunia violacea* Lindl. and the growth of said plant is regulated by a composition consisting essentially of a mixture of IDS free acid and EDDS free acid in a total concentration of $7\times10^{-4}$ gram moles per liter.

16. The process of claim 11 wherein the plant precursor or plant is a germinating seed of a plant.

17. The process of claim 16 wherein the germinating seed of a plant is selected from the group consisting of germinating seeds of monocotyledons and germinating seeds of dicotyledons.

18. The process of claim 17 wherein the range of weight ratios of nitrogen-containing organic compound:germinating seed is in the range of from about $6\times10^{-4}$:1 up to about 0.04:1.

19. The process of claim 16 wherein the germinating seed of a plant is selected from the group consisting of germinating field corn (Zea L., *mays* L.) and germinating snap bean (*Phaseolus vulgaris* L.) seed, the growth of which is regulated by an aqueous solution of one or more alkali metal salts of EDDS in a germinating seed growth regulating concentration and quantity.

20. The process of claim 19 wherein the growth of the germinating seed of a plant is regulated by an aqueous solution containing a nitrogen-containing compound composition consisting of the tetra-sodium salt of EDDS at a concentration of about $10\times10^{-4}$ gram moles per liter.

21. The process of claim 16 wherein the germinating seed of a plant is selected from the group consisting of germinating snap bean (*Phaseolus vulgaris* L.) seed, germinating sweet corn (Zea L. var. *saccharata* Sturt.) seed, and germinating field corn (Zea L., *mays* L.) seed, the growth of which is stimulated by an aqueous nitrogen compound-containing solution selected from the group consisting of (i) one or more ammonium, alkali metal, or ammonium-alkali metal salts of EDDS taken alone, or in combination with one or more ammonium, alkali metal or ammonium-alkali metal salts of IDS and (ii) the free acids of IDS or EDDS, taken alone or in combination, in a germinating seed growth stimulating concentration and quantity.

22. The process of claim 21 wherein the growth of the germinating seed of a plant is stimulated by an aqueous solution containing at least one nitrogen-containing compound selected from the group consisting of (i) the tri-potassium salt of IDS or the tetra-sodium salt of EDDS at a concentration of about $1 \times 10^{-4}$ gram moles per liter and (ii) a mixture of the tri-potassium salt of IDS and the tetra-sodium salt of EDDS at a total concentration of $10 \times 10^{-4}$ gram moles per liter.

23. The process of claim 21 wherein the weight ratio of ammonium, alkali metal or ammonium-alkali metal salts of EDDS to ammonium, alkali metal or ammonium-alkali metal salts of IDS is from about 20:1 up to about 1:20.

24. The process of claim 23 wherein the weight ratio of ammonium, alkali metal or ammonium-alkali metal salts of EDDS to ammonium, alkali metal or ammonium-alkali metal salts of IDS is about 1:1.

25. The process of claim 23 wherein the weight ratio of ammonium, alkali metal or ammonium-alkali metal salts of EDDS to ammonium, alkali metal or alkali metal-ammonium salts of IDS is from about 1:4 up to about 4:1.

26. The process of claims 21 wherein the germinating seed of a plant is the germinating sweet corn (Zea L. var. *saccharata* Sturt.) seed, the growth of which is stimulated by an aqueous solution containing at least one nitrogen-containing compound selected from the group consisting of IDS free acid and EDDS free acid, wherein the nitrogen-containing compound concentration is in the range of from about $5 \times 10^{-4}$ moles per liter up to about $10 \times 10^{-4}$ moles per liter.

27. The process of claim 26 wherein the nitrogen-containing compound concentration is in the range of from about $7 \times 10^{-4}$ gram-moles per liter up to about $8 \times 10^{-4}$ gram moles per liter.

28. The process of claim 26 wherein the range of weight ratios of nitrogen-containing organic compound:germinating seed is from about 0.01:1 up to about 0.04:1.

29. A process for stimulating or regulating, substantially in the absence of any fertilizer or Periodic Table Group IIa or higher group metal cations or chelated metals, the growth of a living, growing plant precursor which is a germinating seed or plant having a degree of maturity of from about >0%, the seedling stage, up to about <100%, the late maturity stage, of full growth consisting of the steps of:

(a) formulating an aqueous plant precursor or plant growth-regulating or stimulating solution consisting essentially of water, substantially free of any fertilizer or any Periodic Table Group IIa or higher Group metal cations or chelated metals; at least one substantially pure nitrogen-containing organic compound selected from the group consisting of IDS, EDDS, ammonium salts thereof, alkali metal salts thereof, ammonium-alkali metal salts thereof and optical isomers thereof; and, optionally, 1H-indole-3-butanoic acid;

(b) providing an adjuvant for said formulated aqueous solution selected from the group consisting of:
 i. carriers;
 ii. surfactants;
 iii. carbon skeleton energy adjuvants;
 iv. vitamin/co-factor adjuvants;
 v. gums;
 vi. anti-microbial agents;
 vii. buffers;
 viii. protective colloids; and
 ix. viscosity modifiers (c) intimately admixing said adjuvant with said formulated aqueous solution in order to form an adjuvant-containing formulated aqueous solution; and (d) applying, in the absence of fertilizer or Periodic Table Group IIa or higher Group metal cations or chelated metals, said adjuvant-containing formulated aqueous solution to said plant precursor or to said plant or to the effective proximity of said plant precursor or said plant, over a period of time and rate, and in a concentration and quantity, such that the plant precursor growth or plant growth is stimulated or regulated.

30. The process of claim 29 wherein the plant precursor or plant is a germinating seed of a plant.

31. The process of claim 30 wherein the germinating seed of a plant is selected from the group consisting of germinating seeds of monocotyledons and dicotyledons.

* * * * *